(12) United States Patent
Song et al.

(10) Patent No.: US 10,617,732 B2
(45) Date of Patent: Apr. 14, 2020

(54) **COMPOSITION INCLUDING EXTRACT OF *DOLICHOS LABLAB* LINNE AS ACTIVE INGREDIENT FOR PREVENTING OR AMELIORATING NON-ALCOHOLIC FATTY LIVER DISEASE**

(71) Applicant: KOREA INSTITUTE OF ORIENTAL MEDICINE, Daejeon (KR)

(72) Inventors: Kwang-Hoon Song, Daejeon (KR); Yun Hee Kim, Gyeonggi-do (KR); Hye Won Lee, Daejeon (KR); A-Rang Im, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 352 days.

(21) Appl. No.: 15/515,896

(22) PCT Filed: Oct. 13, 2015

(86) PCT No.: PCT/KR2015/010745
§ 371 (c)(1),
(2) Date: Mar. 30, 2017

(87) PCT Pub. No.: WO2016/060426
PCT Pub. Date: Apr. 21, 2016

(65) Prior Publication Data
US 2017/0296607 A1 Oct. 19, 2017

(30) Foreign Application Priority Data
Oct. 13, 2014 (KR) ........................ 10-2014-0137399

(51) Int. Cl.
*A61K 36/48* (2006.01)
(52) U.S. Cl.
CPC ........ *A61K 36/48* (2013.01); *A61K 2236/331* (2013.01)
(58) Field of Classification Search
None
See application file for complete search history.

(56) References Cited

FOREIGN PATENT DOCUMENTS

| CN | 101352551 | A | * | 1/2009 |
|---|---|---|---|---|
| CN | 101653211 | B | * | 5/2012 |
| CN | 101653281 | B | * | 10/2012 |
| CN | 104922538 | A | * | 9/2015 |
| KR | 10-0316296 | B1 | | 12/2001 |
| KR | 2003-0031418 | A | | 4/2003 |
| KR | 10-2009-0058366 | A | | 6/2009 |
| KR | 10-2009-0120202 | A | | 11/2009 |
| KR | 10-0929979 | B1 | | 12/2009 |
| KR | 10-2010-0014098 | A | | 2/2010 |
| KR | 10-0952188 | B1 | | 4/2010 |
| KR | 10-1088004 | B1 | | 12/2011 |

OTHER PUBLICATIONS

CN104922538A machine translation from Google Patents (Jun. 21, 2019; patents.google.com). (Year: 2019).*
CN101352551A machine translation from Google Patents (Jun. 21, 2019; patents.google.com). (Year: 2019).*
CN101653281B machine translation from Google Patents (Jun. 21, 2019; patents.google.com). (Year: 2019).*
CN101653211B machine translation from Google Patents (Jun. 21, 2019; patents.google.com). (Year: 2019).*
International Search Report for PCT/KR2015/010745.
Han, Sung Hee et al. "Effects of Jebikong (*Dolichos lablab*) Extract on Serum Lipid Metabolism in Rats Fed a High Fat Diet", Journal of the Korean Society of Food Culture, vol. 28, Issue 4, pp. 409-414, 2013.

* cited by examiner

*Primary Examiner* — Michael Barker
(74) *Attorney, Agent, or Firm* — The PL Law Group, PLLC

(57) ABSTRACT

A health functional food composition and a pharmaceutical composition for preventing or ameliorating a non-alcoholic fatty liver disease include an extract of *Dolichos lablab* Linne as an active ingredient. The extract of *Dolichos lablab* Linne, being an active ingredient, effectively reduces accumulation of triglyceride in hepatocarcinoma cell line (HepG$_2$). Therefore, the compositions are used for functional foods and medicines for the prevention or amelioration of non-alcoholic fatty liver.

18 Claims, 13 Drawing Sheets

COMPOSITION INCLUDING EXTRACT OF *DOLICHOS LABLAB* LINNE AS ACTIVE INGREDIENT FOR PREVENTING OR AMELIORATING NON-ALCOHOLIC FATTY LIVER DISEASE

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/010745, filed Oct. 13, 2015, which claims priority to the benefit of Korean Patent Application No. 10-2014-0137399 filed in the Korean Intellectual Property Office on Oct. 13, 2014, the entire contents of which are incorporated herein by reference.

BACKGROUND

Technical Field

The present invention relates to a health functional food composition and a pharmaceutical composition for preventing or ameliorating a non-alcoholic fatty liver disease including an extract of *Dolichos lablab* Linne as an active ingredient.

Background

The death rate of liver disease in Korea is very high, 23.5 per 100,000 population. As a death reason, in the 40s, liver disease ranks first (41.1/100,000 population), in the 50s, liver disease ranks second (72.4/100,000 population), and in the 30s, liver disease ranks third (10/100,000 population). As such, liver disease is the leading cause of death in the Korean middle-aged population.

As one of the liver diseases, fatty liver refers a liver in which triglyceride, which is not present in normal cells, appears to be abnormally deposited in liver cells. In the case of normal liver, about 5% thereof consists of adipose tissue, and triglyceride, fatty acid, phospholipid, cholesterol, and cholesterol ester are the major components of fat. However, once fatty liver occurs, most components are replaced by triglyceride, and when the amount of triglyceride is 5% or more of the liver weight, the corresponding liver is diagnosed as fatty liver. When the fatty liver becomes worse and fat mass in hepatocyte increases in size, important components of cells including nucleus are pushed to one side, the function of the hepatocyte is lowered, and the expanded hepatocytes due to the accumulated fat in the cells press the microvascular and lymphatic lines between the hepatocytes, resulting in obstacles to circulation of blood and lymph in the liver. In this case, hepatocytes may not receive proper oxygen and nutrient supply, and liver function is deteriorated.

Non-alcoholic fatty liver disease (NAFLD) is defined as the accumulation of fatty acids in the form of triglycerides in hepatic parenchymal cells by 5% or more, rather than a disease by liver damage caused by alcohol. Pathologically, NAFLD is classified as simple steatosis and steatohepatitis accompanied by inflammation. When left untreated for a long time, severe liver disease such as hepatitis, liver fiber and cirrhosis may develop. In Korea, the frequency of non-alcoholic liver disease is increasing due to changes in lifestyle.

Meanwhile, *Dolichos lablab* Linne is called as a sparrow bean, a magpie bean, or *Canavalia gladiata*. Leaves of *Dolichos lablab* Linne are ternate compound leaves and alternately aligned, and stipules thereof are small and triangular, and leaflets thereof are broadly ovate and have sharp leaves, and leaves on trunks are a wide wedge or tacky, with flat edges and hairy on both sides. The flower is butterfly shaped and white, and the seed is white and the number of seeds is 2 to 5.

It has been reported that *Dolichos lablab* Linne has efficacy in books titled with "GUN-WI-WHA-SUP" and "WHA-JONG-SO-SEO" by folk remedies. Korean Patent No. 0316296 discloses the methanol extract of the hyacinth bean leaf has the efficacy of increasing the physiological activity, and Korean Patent No. 0929979 discloses that a herbal composition including *Dolichos lablab* Linne has an effect of reducing the toxicity of liver and kidney induced by administration of an anticancer agent. However, no studies have been reported for the efficacy of *Dolichos lablab* Linne on the non-alcoholic fatty liver.

DETAILED DESCRIPTION OF THE INVENTION

Summary

The present invention has been made in view of the above-mentioned needs, and it has been confirmed that the content of triglycerides is effectively reduced in hepatocytes treated with the extract of *Dolichos lablab* Linne, which is an active ingredient according to the present invention, thereby completing the present invention.

The present invention provides a health functional food composition for preventing or ameliorating non-alcoholic fatty liver disease, the health functional food composition including an extract of *Dolichos lablab* Linne as an active ingredient.

The present invention also provides a pharmaceutical composition for the prevention or treatment of non-alcoholic fatty liver disease, the pharmaceutical composition including an extract of *Dolichos lablab* Linne as an active ingredient.

The present invention also provides a composition for reducing body weight or blood sugar level elevated by a high-fat diet including an extract of *Dolichos lablab* Linne as an active ingredient.

The present invention also provides a method of preventing or treating non-alcoholic fatty liver disease including administering an extract of *Dolichos lablab* Linne to a subject.

The present invention also provides a veterinary composition for the prevention or treatment of fatty liver disease in an animal other than human, the veterinary composition including an extract of *Dolichos lablab* Linne as an active ingredient.

The present invention also provides a feed additive for preventing or ameliorating fatty liver disease in an animal including an extract of *Dolichos lablab* Linne as an active ingredient.

A health functional food composition for preventing or ameliorating a non-alcoholic fatty liver disease (NAFLD) according to the present invention includes, as an active ingredient, an extract of *Dolichos lablab* Linne. The composition inhibits the accumulation of the present invention, and accordingly, may be useful for use as health functional foods and medicines for preventing or ameliorating non-alcoholic fatty liver disease.

BRIEF DESCRIPTION OF THE DRAWINGS

FIG. 1A shows triglyceride contents after staining with Nile Red (AdipoRed), and FIG. 1B shows images of triglycerides after staining with Oil Red O. The control was treated with a free fatty acid-free 5% (w/v) BSA solution.

In FIG. 10A, * and ** indicate that the body weight of the experimental group receiving high-fat diet and the hot water extract of *Dolichos lablab* Linne is significantly decreased compared to that of the high-fat dietary group (HFD); and in FIG. 10B, ## indicates that the liver tissue weight of the high-fat dietary group (HFD) is significantly increased compared to that of the normal control group (CON) (P<0.01), and * and ** indicate that the liver tissue weight of the experimental group (HFD+DLL-Ex) receiving high-fat diet intake and the hot water extract of *Dolichos lablab* Linne is significantly decreased compared to that of the high-fat dietary group (HFD). M100 is a positive control group, which is administered with Milk Thistle extract (100 mg/kg/day) together with a high-fat diet.

DETAILED DESCRIPTION

Figure 1A:
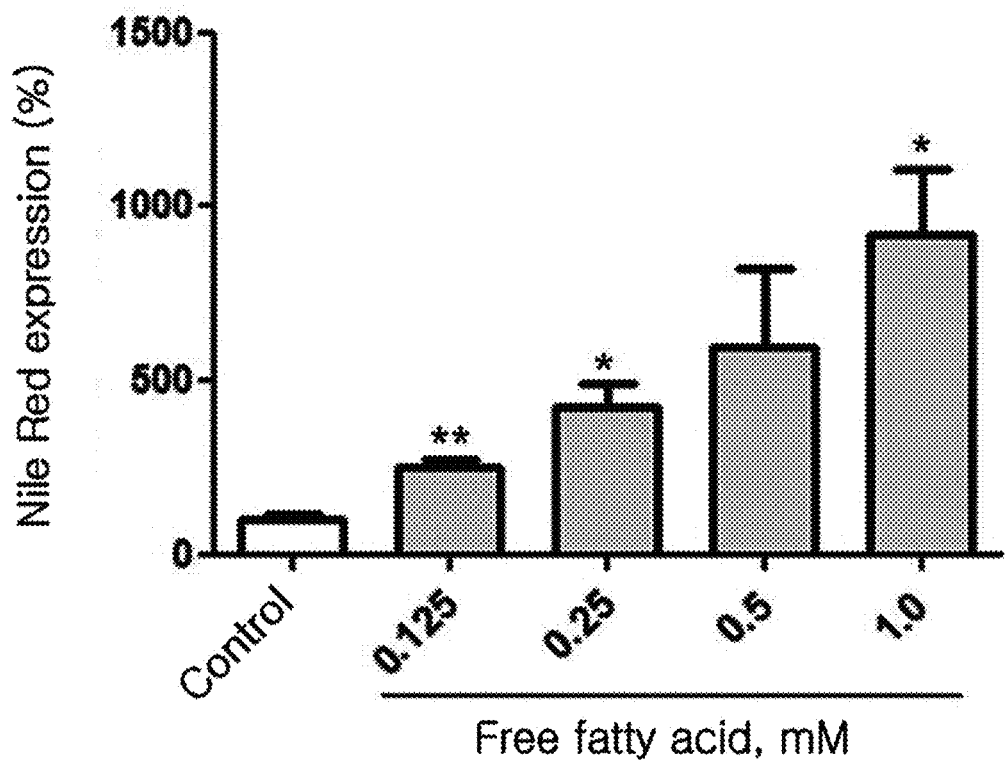
FIGS. 1A and 1B show results obtained by evaluating triglyceride contents after hepatocarcinoma cell line (HepG$_2$) is treated with free fatty acids (0.125, 0.25, 0.5 and 1.0 mM) mixed with oleate and palmitate at a concentration ratio of 2:1.

The present invention relates to a health functional food composition for preventing or ameliorating a non-alcoholic fatty liver including an extract of *Dolichos lablab* Linne as an active ingredient.

The *Dolichos lablab* Linne extract may be obtained by using a conventional extraction solvent known in the art. Examples of the extraction solvent are water, anhydrous or water-containing low alcohol having 1 to 4 carbon atoms (e.g. methanol, ethanol, propanol, butanol, n-propanol, isopropanol, and n-butanol), a mixed solvent including the low alcohol and water, acetone, ethyl acetate, chloroform, 1,3-butylene glycol, hexane, diethyl ether, and butyl acetate. In one embodiment, water or ethanol may be used. In one embodiment, water may be used.

In the case of hot water extraction using the above-mentioned water, water is added in an amount of 5 to 10 times the weight of *Dolichos lablab* Linne and heated at the temperature of 90° C. to 110° C. for 2 to 3 hours for extraction. The extraction solution is filtered through filter paper and then freeze-dried, but embodiments are not limited thereto.

In the case of ethanol extraction, 80% ethanol is added in an amount of 5 to 10 times the weight of *Dolichos lablab* Linne, and *Dolichos lablab* Linne is dipped therein at the temperature of 20° C. to 25° C. for 22 to 24 hours. The extraction solution is filtered through filter paper and then freeze-dried, but embodiments are not limited thereto.

The *Dolichos lablab* Linne extract reduces the triglyceride content in the liver tissue, and the non-alcoholic fatty liver disease is any one selected from the non-alcoholic simple fatty liver, non-alcoholic fatty hepatitis, and non-alcoholic liver cirrhosis. However, examples of the non-alcoholic fatty liver disease are not limited thereto.

The amount of the extract of the *Dolichos lablab* Linne may be in a range of 0.1 wt % to 10 wt % based on the total weight of the composition. However, embodiments of the present invention are not limited thereto. The composition according to the present invention may be added to food for the prevention or amelioration of non-alcoholic fatty liver disease to manufacture health functional food. Examples of the health functional food are, but not particularly limited to, health functional foods, nutritional supplements, nutritional supplements, pharmafood, health food, nutraceutical, designer food, food additives, etc. In one embodiment, the health functional food may be meat, sausage, bread, chocolate, candy, snack, confectionery, pizza, instant noodles, other noodles, gums, dairy products including ice cream, various soups, drinks, tea, functional drinks, an alcoholic beverage, a vitamin complex, and the like. In this regard, the adding is appropriately performed according to a conventional method, and the amount of the composition to be added may be appropriately determined according to the purpose of use (prevention, health, or therapeutic treatment).

The composition according to the present invention may further include various components other than the active ingredient. The various components may be, but not particularly limited to, various nutrients, vitamins, electrolytes, flavors, colorants, pectinic acids or salts thereof, alginic acids or salts thereof, organic acids, protective colloid thickening agents, pH adjusting agents, stabilizers, preservatives, glycerin, alcohols, carbonating agents used in carbonated drinks and the like. The composition according to the present invention may further include natural fruit juices, fruit juice drinks, and the pulp for vegetable drinks to provide palatability and/or functionality, and these ingredients may be used independently or in combination.

The present invention also relates to a pharmaceutical composition for the prevention or treatment of non-alcoholic fatty liver disease, the pharmaceutical composition including an extract of *Dolichos lablab* Linne as an active ingredient.

The extract of *Dolichos lablab* Linne may be obtained by using a conventional extraction solvent known in the art. Examples of the extraction solvent are water, anhydrous or water-containing low alcohol having 1 to 4 carbon atoms (e.g. methanol, ethanol, propanol, butanol, n-propanol, isopropanol, and n-butanol), a mixed solvent including the low alcohol and water, acetone, ethyl acetate, chloroform, 1,3-butylene glycol, hexane, diethyl ether, and butyl acetate. In one embodiment, water or ethanol may be used. In one embodiment, water may be used.

In the case of hot water extraction using the above-mentioned water, water is added in an amount of 5 to 10 times the weight of *Dolichos lablab* Linne and heated at the temperature of 90° C. to 110° C. for 2 to 3 hours for extraction. The extraction solution is filtered through a filter paper and then freeze-dried, but embodiments are not limited thereto.

In the case of ethanol extraction, 80% ethanol is added in an amount of 5 to 10 times the weight of *Dolichos lablab* Linne, and *Dolichos lablab* Linne is dipped therein at the temperature of 20° C. to 25° C. for 22 to 24 hours. The extraction solution is filtered through a filter paper and then freeze-dried, but embodiments are not limited thereto.

The extract of *Dolichos lablab* Linne reduces the triglyceride content in the liver tissue, and the non-alcoholic fatty liver disease is any one selected from the non-alcoholic simple fatty liver, non-alcoholic fatty hepatitis, and non-alcoholic liver cirrhosis. However, examples of the non-alcoholic fatty liver disease are not limited thereto.

The pharmaceutical composition according to the present invention may include a pharmaceutically acceptable carrier. The pharmaceutically acceptable carrier to be included in the pharmaceutical composition according to an embodiment of the present invention may be any one that is conventionally used in preparing formulations. Examples of the pharmaceutically acceptable carrier are a saline solution, sterilized water, a Ringer's solution, a buffered saline solution, a dextrose solution, a maltodextrin solution, glycerol, ethanol, lactose, dextrose, sucrose, sorbitol, mannitol, starch, acacia rubber, calcium phosphate, alginate, gelatin, calcium silicate, microcrystalline cellulose, polyvinylpyrrolidone, cellulose, syrup, methylcellulose, methylhydroxybenzoate, propylhydroxybenzoate, talc, magnesium stearate, and mineral oil, but are not limited thereto.

The pharmaceutical composition according to the present invention may further contain, in addition to these components, an antioxidant, a buffer, a bacteriostatic agent, a diluent, a surfactant, a binder, a lubricant, a wetting agent, a sweetener, a flavoring agent, an emulsifier, a suspending agent, a preservative, or the like.

The pharmaceutical composition according to the present invention may be administered orally or parenterally. In one embodiment, the pharmaceutical composition may be administered orally. The appropriate dosage of the pharmaceutical composition according to the present invention may vary depending on factors such as a formulation method, an administration method, age, body weight, gender, pathological conditions, food, administration time, route of administration, excretion rate, or response susceptibility. The dosage of the pharmaceutical composition according to the present invention may be in a range of 0.001 mg/kg to 100 mg/kg on an adult basis.

The pharmaceutical composition according to the present invention may be formulated into a unit dosage form or a multi-dose container by using a pharmaceutically acceptable carrier and/or excipient according to a method which can be easily carried out by those having ordinary skill in the art. In this regard, a formulation available herein may be a solution, a suspension, a syrup, or an emulsion in oils or aqueous media, or extract, powder, a granule, a tablet, or a capsule, and the formulation may additionally contain a dispersing agent or a stabilizing agent.

The present invention also relates to a composition for reducing body weight or blood sugar level elevated by a high-fat diet including an extract of *Dolichos lablab* Linne as an active ingredient.

The present invention also relates to a method of preventing or treating non-alcoholic fatty liver disease, the method including administering an extract of *Dolichos lablab* Linne to a subject.

The subject includes all animals, including those with a non-alcoholic fatty liver disease and those having the likelihood to develop the non-alcoholic fatty liver disease.

The present invention also relates to a veterinary composition for the prevention or treatment of fatty liver disease in an animal other than human, the veterinary composition including an extract of *Dolichos lablab* Linne as an active ingredient.

The veterinary composition including the extract of *Dolichos lablab* Linne according to the present invention may further include suitable excipients and diluents according to conventional methods. Excipients and diluents suitable for use in the veterinary composition including the extract of *Dolichos lablab* Linne according to the present invention include lactose, dextrose, sucrose, sorbitol, mannitol, xylitol, erythritol, maltitol, starch, *Acacia* rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, cetyl alcohol, stearyl alcohol, liquid paraffin, sorbitan monostearate, polysorbate 60, methylparaben, propylparaben, and mineral oil.

The veterinary composition including the extract of *Dolichos lablab* Linne according to the present invention may further include a filler, an anti-coagulant, a lubricant, a wetting agent, a spice, an emulsifier, a preservative, and the like. The veterinary composition may be formulated by using such methods known in the art that provide rapid, sustained or delayed release of the active ingredient after administration to the animal. A formulation available herein may be powder, a granule, a tablet, a capsule, a suspension, an emulsion, a solution, syrup, aerosol, a soft or hard gelatin capsule, a suppository, a sterile injectable solution, a sterile external preparation, and the like.

The dosage of the veterinary composition according to the present invention may vary depending on the age, gender, and body weight of the animal, and may be administered in an amount of 0.1 to 100 mg/kg once or several times a day. The dosage may vary depending on an administration route, gender, body weight, age, and the like. Accordingly, the dosage is not intended to limit the scope of the present invention.

The present invention also relates to a feed additive for preventing or ameliorating fatty liver disease in an animal including an extract of *Dolichos lablab* Linne as an active ingredient.

The feed additive may be in the form of a high concentrate, powder or granulate containing 20 to 90 wt % of the extract of *Dolichos lablab* Linne.

The feed additive according to the present invention may further include at least one selected from: organic acids such as citric acid, fumaric acid, adipic acid, lactic acid, or malic acid; a phosphate such as sodium phosphate, potassium phosphate, acid pyrophosphate, or polyphosphate (polymerized phosphate); and natural antioxidants such as polyphenol, catechin, alpha-tocopherol, rosemary extract, vitamin C, green tea extract, licorice extract, chitosan, tannic acid, and phytic acid.

The animal feed additive containing the extract of *Dolichos lablab* Linne according to the present invention and a feed including the animal feed additive may be supplemented with, as an auxiliary component, amino acids, inorganic salts, vitamins, antibiotics, antibacterial substances, antioxidants, antifungal enzymes, digestion and absorption facilitators, growth promoting agents, disease prevention agents, or the like.

The feed additive may be administered to the animal, alone or in combination with other feed additives in an edible carrier. The feed additives may also be easily administered as a top dressing or may be mixed directly with the animal feed, or separately from the feed, in separate oral formulations, by injection, transdermal or in combination with other ingredients. A single daily dose or a divided daily dose known in the art may be used. When the feed additive is administered separately from the animal feed, the dosage form of the extract, as known in the art, may be prepared in an immediate release or sustained release formulation in combination with a non-toxic pharmaceutically acceptable edible carrier. Such edible carriers may be solid or liquid, for example, corn starch, lactose, sucrose, soy flakes, peanut oil, olive oil, sesame oil, and propylene glycol. When a solid carrier is used, the dosage form of the extract may be a top-dressing in the form of tablet, capsule, powder, troche, lozenge, or emulsion or in a finely divided form. When a liquid carrier is used, the dosage form of the extract may be in the form of a soft gelatin capsule, a syrup or liquid suspension, an emulsion, or a solution. The dosage form may contain adjuvants such as preservatives, stabilizers, wetting or emulsifying agents, solution promoters, and the like. An animal feed which includes the feed additive including the extract of *Dolichos lablab* Linne may be any protein-containing organic flour that is used to meet animal dietary needs. The protein-containing flour usually consists mainly of corn, soy flour or a mixture including corn and soy flour. The feed additive may be added to the animal feed by dipping, spraying or mixing.

The veterinary composition or feed additive according to the present invention may be applied to the companion animal's diet.

Hereinafter, embodiments of the present invention will be described in more detail with reference to Examples. It is to be understood by those skilled in the art that these embodiments are only for illustrative purpose and that do not limit the scope of the present invention.

[Reagent]

1) Preparation of Stock Solution of Oil Red O (Sigma (Cat #0-0625), FW 408.5)

0.35 g of Oil Red O was dissolved in 100 ml of isopropanol and the resultant solution was filtered using a 0.2 μm filter and stored at room temperature.

2) Preparation of Oil Red O Working Solution 6 ml of the Oil Red O stock solution and 4 ml of ddH$_2$O were mixed and then the resultant solution was filtered using a 0.2 μm filter and left at room temperature for 20 minutes.

3) Preparation of 10% Formalin Solution

A stock solution (37%, Merck, Cat # K36658003), which had been prepared by diluting 27 ml of an undiluted formalin solution in 63 ml of ddH$_2$O, was mixed with 10 ml of 10×PBS.

4) 100% Isopropanol (Merck, Cat # K36543834) was Used as a Blank.

5) Preparation of 60% Isopropanol

60% isopropanol was prepared by mixing 6 ml of 100% isopropanol and 4 ml of ddH$_2$O.

Example 1. Culture of Hepatocarcinoma Cell Line (HepG$_2$)

Hepatocarcinoma cell line (HepG$_2$) used herein was purchased from ATTC (American Type Culture Collection) Inc. Hepatocarcinoma cell line (HepG$_2$) was cultured in DMEM (Dulbecco's modified eagle's medium) containing 10% FBS and 1% penicillin-streptomycin. The cells were cultured in a 5% CO$_2$ incubator at 37° C. and cultured cells were seeded in a population of cells (3×10$^4$ cells/5000 well) in a 24-well plate.

After placed in a 24-well plate, the cells were used when the cells were completely attached to 24 wells to form a certain shape and reached a confluence of 75%.

Example 2. Preparation of Free Fatty Acid (FFA)

(1) Preparation of 100 mM Palmitate (Sigma P-0500) Stock Solution and 100 mM Olate (Sigma O-75010) Stock Solution These stock solutions were prepared by using 0.1 M NaOH solution as a solvent at 70° C. The solutions were filtered using a 0.2 μm filter, and then sterilized.

(2) Preparation of Free Fatty Acid-Free 5% (w/v) BSA (Sigma A-6003) Solution

This solution was prepared by using deionized water (ddH$_2$O) as a solvent, sterilized and stored at 4° C. in a refrigerator.

(3) Preparation of 5 mM Mixed Fatty Acid Stock Solution Including Olate and Palmitate at a Concentration Ratio of 2:1

At 60° C., 10 mL of a fatty acid stock solution having 5 mM of fatty acid concentration was prepared from each of the stock solutions prepared in (1), by using the free fatty acid-free 5% (w/v) BSA solution dissolved in the deionized water prepared in (2) as a solvent. 165 μl (1.65 mM) of palmitate and 330 μl (3.3 mM) of oleate were obtained from 100 mM palmitate stock solution and 100 mM olate stock solution prepared in (1) above, and added dropwise to 9,505 μl of the 5% (w/v) BSA solution while vortexing. Thereafter, the mixture was cooled to room temperature and then filtered through a 0.2 μm filter (the mixed solutions retained their stability at −20° C. even after 3 to 4 weeks of storage).

(4) Preparation of 1 mM Mixed Free Fatty Acid Containing 1% (w/v) BSA

In a sterile environment, DMEM containing the 5% (w/v) BSA-containing 5 mM mixed free fatty acid (free fatty acid mixed with olate and palmitate at a concentration ratio of 2:1) solution (10 ml) prepared in the above (3) and 0.5% FBS/1% penicillin-streptomycin was mixed with a growth medium (40 ml) containing 495 μl of NaOH to prepare 50 ml of a mixed fatty acid stock solution in which a final concentration of FFA was 1 mM and a final concentration of BSA was 1% (w/v).

(5) Preparation of BSA Control Solution

DMEM containing 10 ml of 5% FFA-free BSA solution and 40 ml of 0.5% FBS/1% penicillin-streptomycin was mixed with a growth medium containing 495 μl of NaOH in such a way that the final volume was 50 ml.

(6) Preparation of Positive Control Solution

10 μM to 100 μM of 18 beta-glycyrrhetinic acids was used as a positive control.

Example 3. Preparation of Extract of *Dolichos lablab* Linne (1) Preparation of Hot water extract of *Dolichos lablab* Linne 2 l of water was added to 200 g of *Dolichos lablab* Linne, heated at 90° C. to 100° C. for 2 to 3 hours, and then the extract thereof was filtered therefrom. Then, the result was dried under reduced pressure by using a freezing dryer to obtain the hot water extract of *Dolichos lablab* Linne, which was dissolved in 10% (v/v) DMSO for use in the experiment.

(2) Preparation of Ethanol Extract of *Dolichos lablab* Linne 2 l of 80% ethanol was added to 200 g of *Dolichos lablab* Linne, *Dolichos lablab* Linne was dipped therein at a temperature of 20° C. to 25° C. for 22 to 24 hours, and then the extract thereof was filtered therefrom. Next, the extract was concentrated by using a vacuum concentrator and dried under reduced pressure using a freezing dryer. The resulting ethanol extract was dissolved in 10% (v/v) DMSO to be used for the experiment.

Example 4. Evaluation of Triglyceride Content (1) Nile Red (AdipoRed) Staining Assay Hepatocarcinoma cell line (HepG$_2$)-containing medium was treated with 1 mM free fatty acid (FFA), and after 24 hours, the medium was gently suctioned.

An AdipoRed solution (prepared by dissolving 300 μl of AdipoRed in 10 ml of PBS) was added in portions per 500 μl/well at a temperature of 37° C., and then, the result was shaken for 15 minutes under the dark condition at room temperature. During this process, the plate was wrapped in aluminum foil to minimize photobleaching of the dye.

After the reaction was completed, the cells were subjected to a spectrophotometer to measure the excitation at 485 nm and the emission at 572 nm.

(2) Oil Red O Staining Assay

After the medium was removed from the Hepatocarcinoma cell line (HepG$_2$), the cells were washed with 0.5 ml of PBS buffer solution, and the PBS buffer solution was completely removed therefrom. Then, 0.5 ml of 10% formalin was added thereto at room temperature and the resultant cells were incubated for 10 minutes.

After removing the formalin and adding 0.5 ml of fresh formalin, the cells were incubated for at least 1 hour (the cells can be stored in a formalin solution for several days before staining, and needs to be wrapped with an aluminum foil and parafilm to prevent the cells from being dried).

Thereafter, the formalin was removed by using a pipette and then the cells were washed twice with 0.5 ml of ddH$_2$O. The cells were washed with 60% isopropanol for 5 minutes at room temperature. The cells were allowed to dry completely at room temperature (it is possible to dry them using a dryer).

0.5 ml of an Oil Red O solution was added to the dried cells, which was then incubated at room temperature for 10 minutes. Then, the Oil Red O solution was removed therefrom, immediately followed by 4 times of washing using ddH$_2$O. The debris of the staining solution was removed as much as possible, and images of the cells were obtained using a fluorescence microscope.

To the cells that had been completely dried, 0.5 ml of Oil Red O staining solution prepared by using 100% of isopropanol in a dry state was added. Then, the cells were incubated for 10 minutes with gentle shaking. At this time, the resultant solution was mixed with a pipette up and down so that the cells were stained well with Oil Red O. Then, the mixture was transferred to a 96-well plate and the OD was measured at 500 nm. The OD value of 100% isopropanol was measured and used as a reference value (0 point).

4.1. Confirming of Increase in Triglyceride Content Due to Free Fatty Acid in Hepatocarcinoma Cell Line (HepG$_2$)

To confirm the efficacy of the extract of *Dolichos lablab* Linne on non-alcoholic fatty liver (NAFLD), a cellular non-alcoholic fatty liver model induced by free fatty acid was used as a cellular model.

Figure 1B:
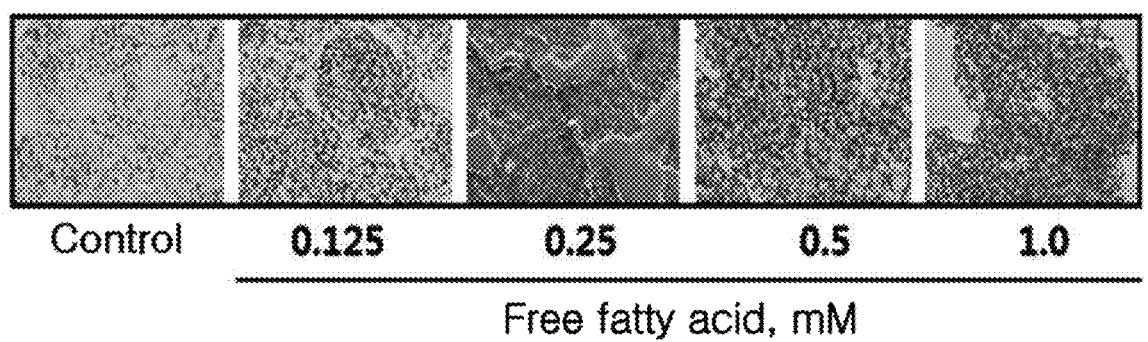

The hepatocarcinoma cell line (HepG$_2$) was treated with each of 0.125, 0.25, 0.5, and 1.0 mM free fatty acid mixed with oleic acid and palmitic acid at a weight ratio of 2:1, and the changes in triglyceride content were measured by Nile Red staining assay and Oil-red-O staining. The results of the staining assays showed that the triglyceride content was increased in proportion to the concentration increase of free fatty acid (FIGS. 1A and 1B).

4.2. Confirming of Effect of Extract of *Dolichos lablab* Linne on Decrease in Triglyceride Generated by Treating Hepatocarcinoma Cell Line (HepG$_2$) with Free Fatty Acid First, 18 beta-glycyrrhetinic acid (0, 10, 30, 50 and 100 μM), known as a substance that is effective for decomposing triglycerides, was used to confirm the decrease in the triglyceride content in cells.

Figure 2:
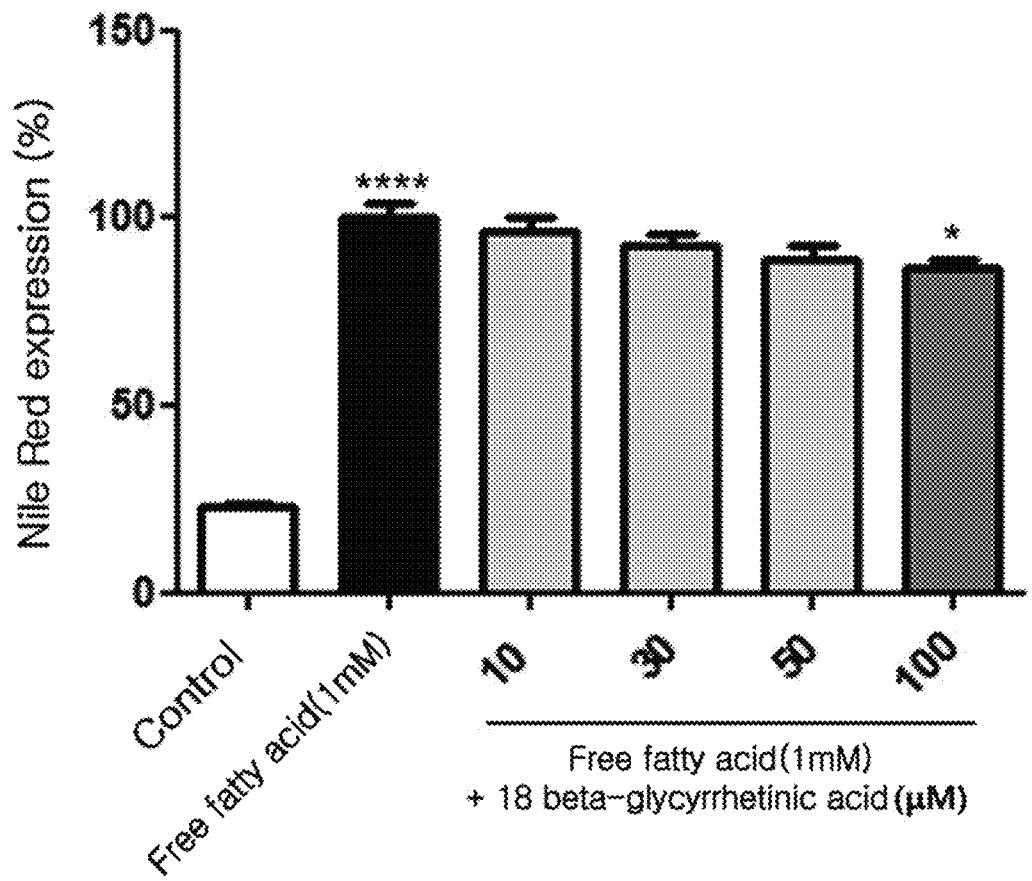
FIG. 2 shows results obtained by evaluating triglyceride contents after staining with Nile Red to confirm a decrease in triglyceride generated by treating hepatocarcinoma cell line (HepG$_2$) with 1 mM free fatty acid due to 18 beta-glycyrrhetinic acid, which is a positive control. The control was treated with a free fatty acid-free 5% (w/v) BSA solution.
Figure 3:
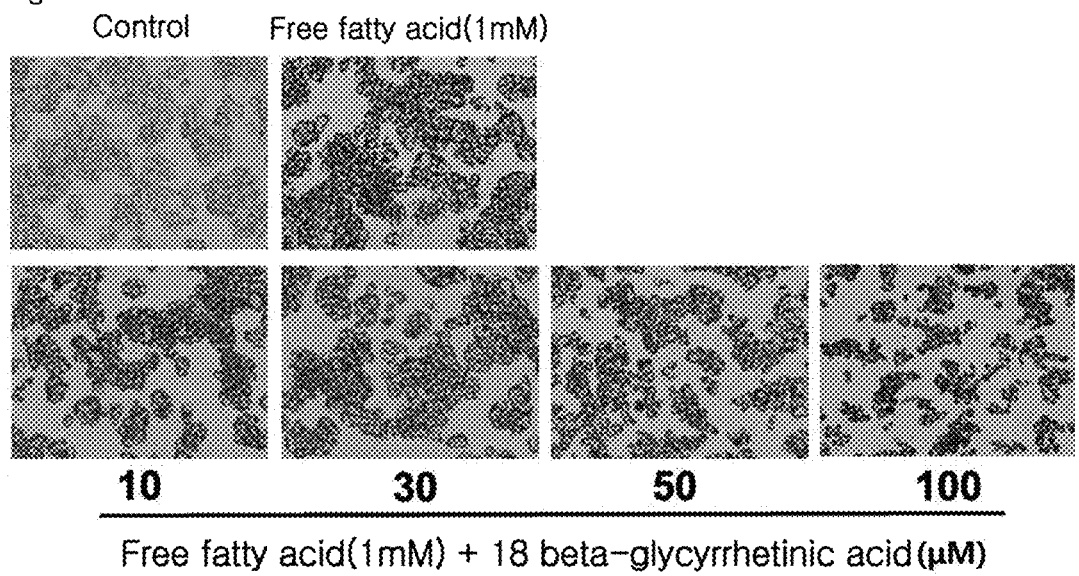
FIG. 3 shows images of triglyceride after staining with Oil Red O to confirm a decrease in triglyceride generated by treating hepatocarcinoma cell line (HepG$_2$) with 1 mM free fatty acid due to 18 beta-glycyrrhetinic acid, which is a positive control. The control was treated with a free fatty acid-free 5% (w/v) BSA solution.

As shown in FIG. 2, results of Nile Red staining assay performed on the hepatocarcinoma cell line treated with 18 beta-glycyrrhetinic acid (0, 10, 30, 50 and 100 μM) showed that 18 beta-glycyrrhetinic acid is effective in reducing the content of triglyceride by about 10% to about 15%. Even from the images showing Oil-red-O staining results, it had been confirmed that the higher concentration of 18 beta-glycyrrhetinic acid, the smaller content of triglyceride (FIG. 3).

Figure 4:
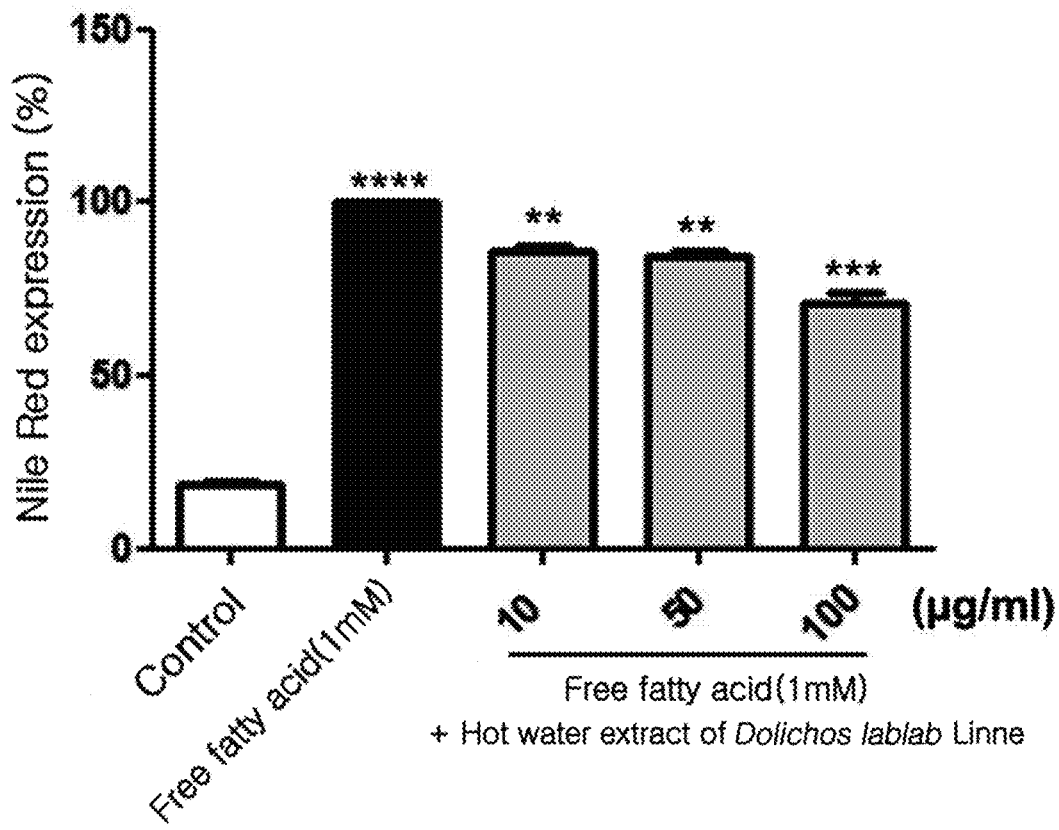
FIG. 4 shows Nile Red staining assay results to confirm a decrease in triglyceride generated by treating hepatocarcinoma cell line (HepG$_2$) with 1 mM of free fatty acid due to the hot water extract of *Dolichos lablab* Linne. The control was treated with a free fatty acid-free 5% (w/v) BSA solution.
Figure 5:
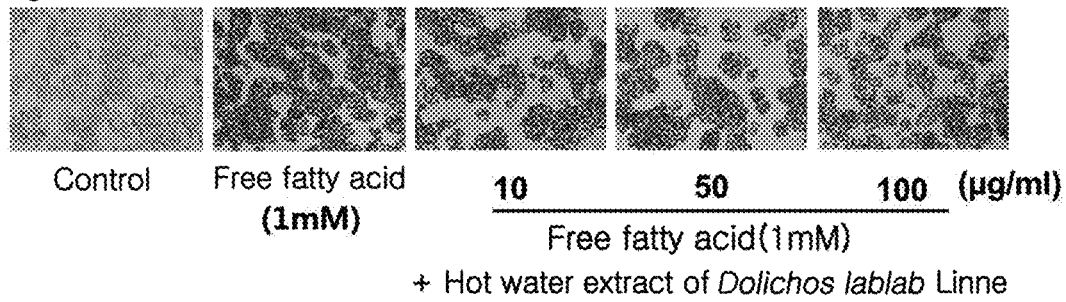
FIG. 5 shows images of triglyceride obtained by Oil Red O staining assay to confirm a decrease in triglyceride generated by treating hepatocarcinoma cell line (HepG$_2$) with 1 mM of free fatty acid due to the hot water extract of *Dolichos lablab* Linne. The control was treated with a free fatty acid-free 5% (w/v) BSA solution.

Thereafter, the degree of reduction in the triglyceride produced by treating the hepatocarcinoma cell line (HepG$_2$) with 1 mM of the mixed free fatty acid including olate and palate (2:1) due to the extract of *Dolichos lablab* Linne was evaluated by Nile Red staining assay and Oil-red-O staining assay. Results of the staining assays showed that about 28% of the triglyceride was reduced in a concentration-dependent manner at the concentrations of 10, 50 and 100 μg/ml of the hot water extract of *Dolichos lablab* Linne (FIGS. 4 and 5).

Figure 6:
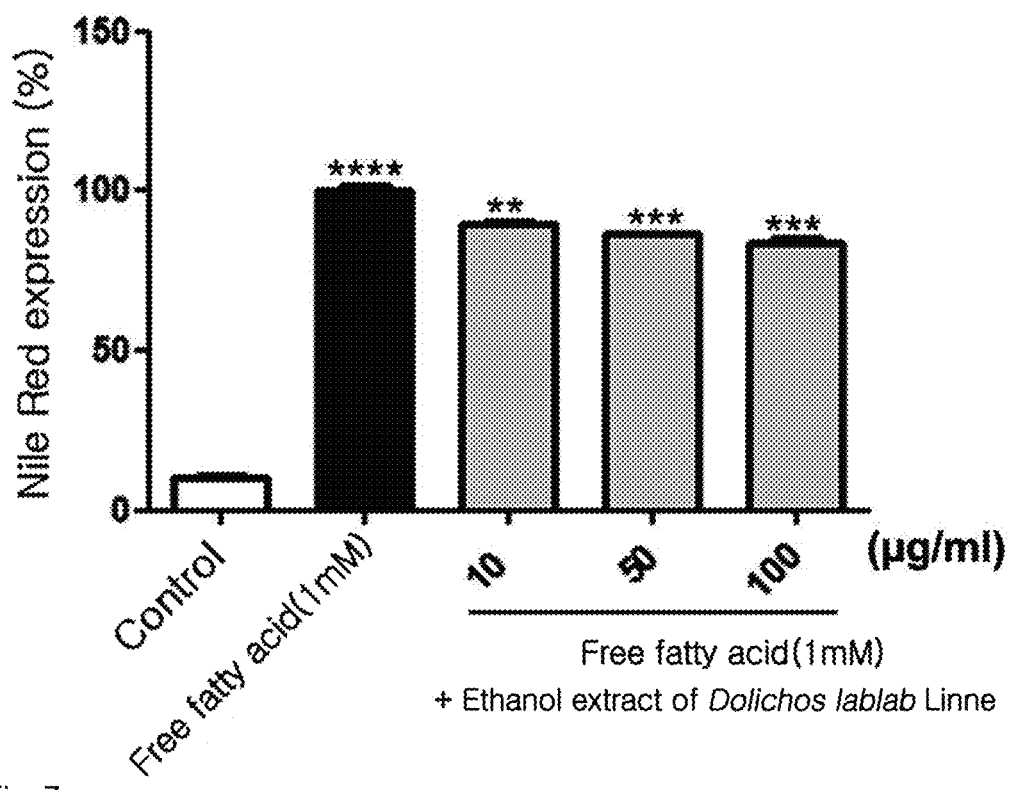
FIG. 6 shows Nile Red staining assay results to confirm a decrease in triglyceride generated by treating hepatocarcinoma cell line (HepG$_2$) with 1 mM of free fatty acid due to the ethanol extract of *Dolichos lablab* Linne. The control was treated with a free fatty acid-free 5% (w/v) BSA solution.
Figure 7:
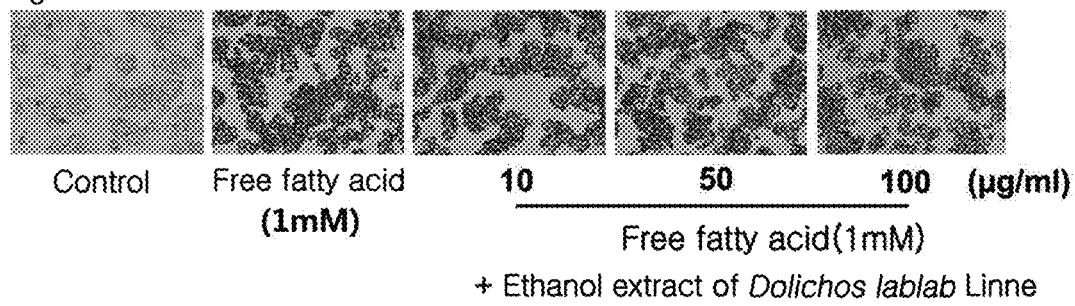
FIG. 7 shows images of triglyceride obtained by Oil Red O staining assay to confirm a decrease in triglyceride generated by treating hepatocarcinoma cell line (HepG$_2$) with 1 mM of free fatty acid due to the ethanol extract of *Dolichos lablab* Linne. The control was treated with a free fatty acid-free 5% (w/v) BSA solution.

In addition, although the ethanol extract of *Dolichos lablab* Linne showed a smaller decrease in the triglyceride content than the hot water extract of *Dolichos lablab* Linne, as shown in FIGS. 6 and 7, results of Nile Red staining assay Oil-red-O staining assay showed that the ethanol extract is effective in decreasing the triglyceride content by 10% to 15%.

4.3. Comparison of Triglyceride Content Reducing Effect of Hot Water Extract of *Dolichos* and Extract of Legumes (Soybean, Seoritae, Mung Bean and Pea)

Figure 9:
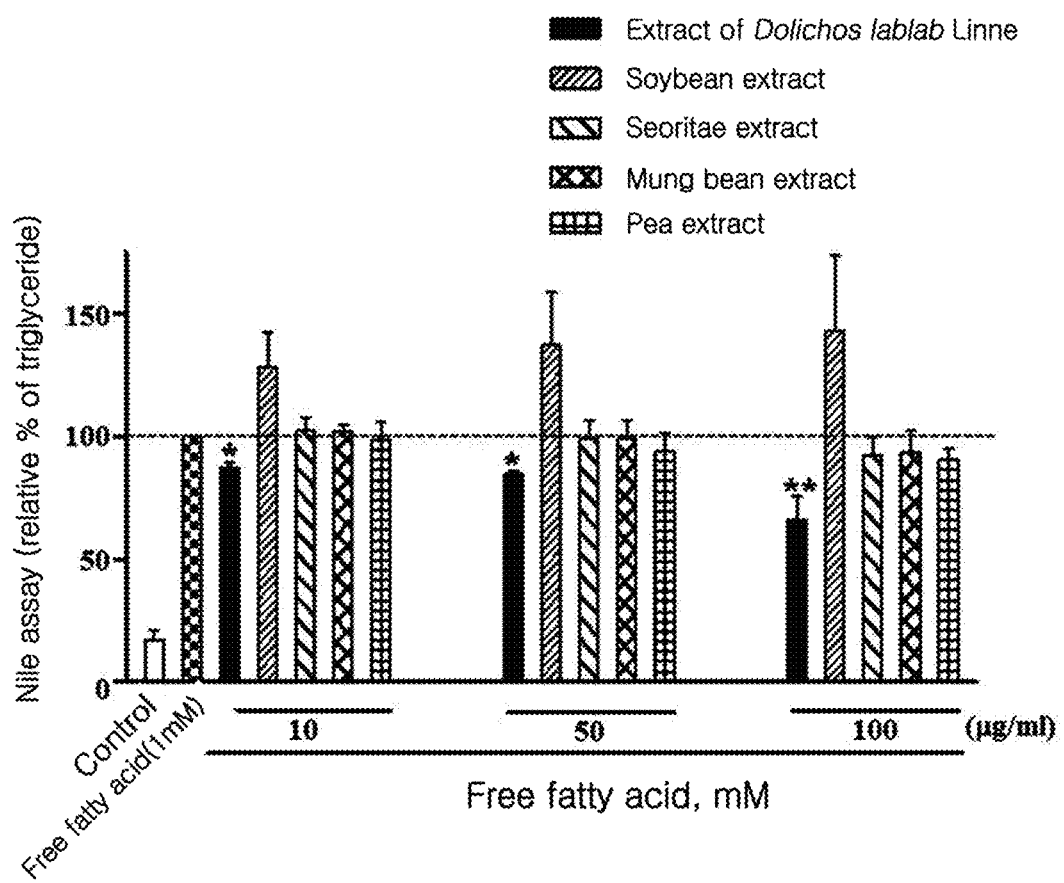
FIG. 9 shows results of Nile Red staining assay conducted on the hot water extract of *Dolichos lablab* Linne and, as a control, soybean extract, Seoritae extract, mung bean extract, and pea extract to compare a decrease in triglyceride content thereof according to an embodiment of the present invention. The control was treated with a free fatty acid-free 5% (w/v) BSA solution, having the relative value of 100% corresponding to a triglyceride content obtained when 5% (w/v) BSA solution included 1 mM free fatty acid.

To confirm whether, like the hot water extract of *Dolichos lablab* Linne, other legumes also have the effect of reducing the triglyceride content in hepatocytes, the extracts of soybean, Seoritae (green kernel black bean), mung bean and pea were used as a control, and Nile Red assay was performed thereon to analyze changes in the content of triglycerides. As shown in FIG. 9, the Nile Red assay results of legumes other than the extract of *Dolichos lablab* Linne showed no effect of reducing the triglyceride, and only the extract of *Dolichos lablab* Linne showed a significant decrease in triglyceride (FIG. 9).

Example 5. Cytotoxicity of the Extract of *Dolichos lablab* Linne

Figure 8:
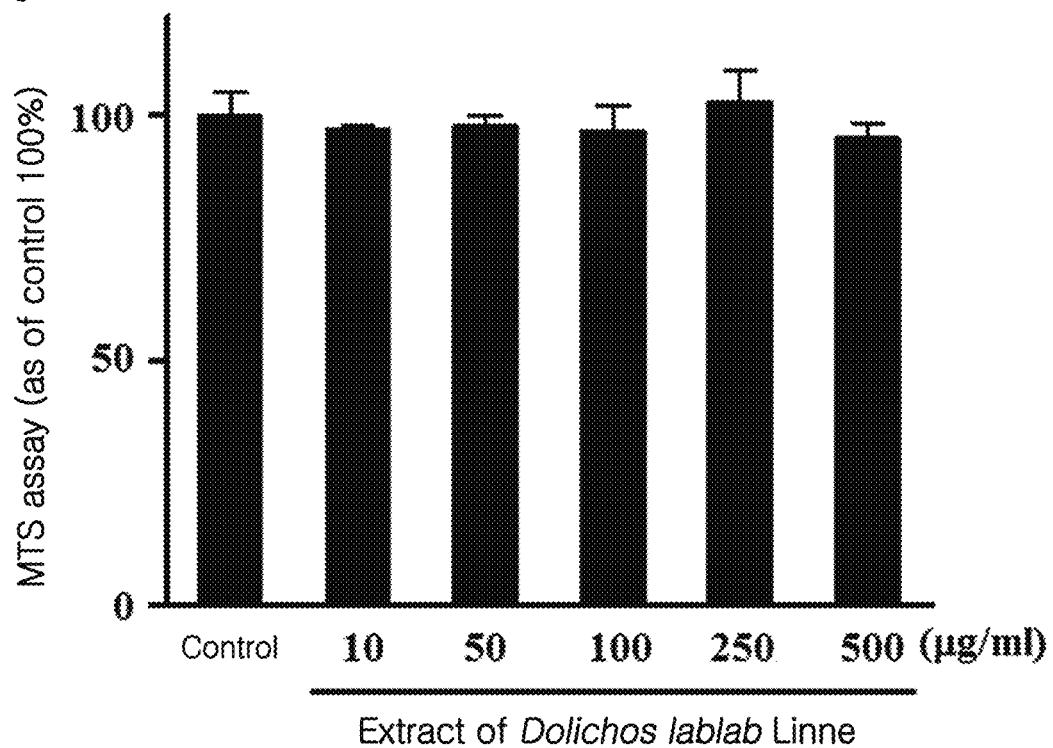
FIG. 8 show results of MTS assay conducted to examine the cytotoxicity of the hot water extract of *Dolichos lablab* Linne according to an embodiment of the present invention. The control was treated with a free fatty acid-free 5% (w/v) BSA solution.

The MTS assay was performed to confirm the cytotoxicity of the hot water extract of *Dolichos lablab* Linne according to the present invention. The MTS assay was carried out according to a conventional method. The results showed that, as shown in FIG. 8, even at a high concentration of 500 μg/ml, the cell viability was hardly changed. Accordingly, it was confirmed that the hot water extract of *Dolichos lablab* Linne had no cytotoxicity.

Example 6. Confirmation of the Effect of Extract of *Dolichos lablab* Linne on High-Fat Diet Mouse (1) Breeding of Experimental Animals Experimental animals were purchased from Sam Taco Co., Ltd., 120: male C57BL/6J mice at 8 weeks of age and adapted for 2 weeks. According to the randomized complete block design, the mice were classified as a normal diet control (CON, 10% fat), a high-fat diet control (HFD, 60% fat), a group receiving a high-fat diet and administered with the hot water extract of *Dolichos lablab* Linne prepared in (1) of Example 3 (25 mg/kg/day, 50 mg/kg/day, 100 mg/kg/day), and a positive control receiving a high-fat diet and administered with Milk Thistle extract (100 mg/kg/day), and each group was bred for 9 weeks, and given with water and experimental diet freely. Each group consisted of twenty mice. For each group, the high-fat diets and extracts were fed orally for 9 weeks daily. Changes in body weight were measured weekly for 9 weeks. Dietary intake, liver weight, and abdominal fat weight were measured. The temperature and humidity of the laboratory animal facilities used for these experiments were maintained at 22±1° C. and 50±5%, respectively, and the contrast therein was adjusted at 12 hour intervals. 10% normal diet and 60% high-fat diet were purchased from the Central Laboratory Animals, Inc.

Figure 10A:
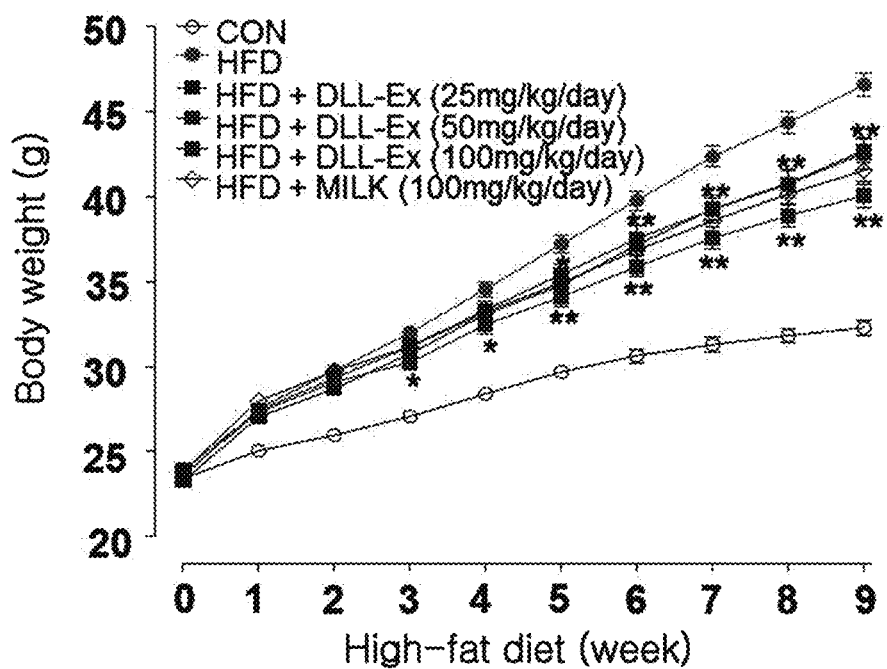
FIGS. 10A and 10B show results obtained by evaluating the effect of the hot water extract of *Dolichos lablab* Linne according to an embodiment of the present invention with respect to a high-fat diet on the increase in body weight (FIG. 10A) and the increase in liver tissue weight (FIG. 10B) of mice. CON is a normal control group, HFD is a high-fat dietary group having fatty liver induced by a high-fat diet, and HFD+DLL-Ex is an experimental group receiving high-fat diet and 25, 50, 100 (mg/kg/day) of the hot water extract of *Dolichos lablab* Linne.

(2) Changes in Body Weight, Liver Tissue, Total Fat, Abdominal Subcutaneous Fat, Epididymal Fat Tissue, and Small Intestinal Fat Tissue The effects of the hot water extract of *Dolichos lablab* Linne prepared in (1) of Example 3 on the weight gain of the mice due to the high-fat diet was evaluated. Results showed that, compared with the high-fat dietary group, the group treated with the high-fat diet and the hot water extract of *Dolichos lablab* Linne prepared in (1) of Example 3 had a significantly low body weight. In particular, the increase in body weight was significantly reduced in the group treated with 100 mg/kg/day of the hot water extract of *Dolichos lablab* Linne (FIG. 10A).

The effects of the hot water extract of *Dolichos lablab* Linne prepared in (1) of Example 3 on the decrease in the liver tissue weight increased due to the high-fat diet was evaluated. Results showed that, compared with the high-fat dietary group, the group treated with the high-fat diet and the hot water extract of *Dolichos lablab* Linne according to the present invention had a substantial decrease in the liver tissue weight.

Figure 10B:
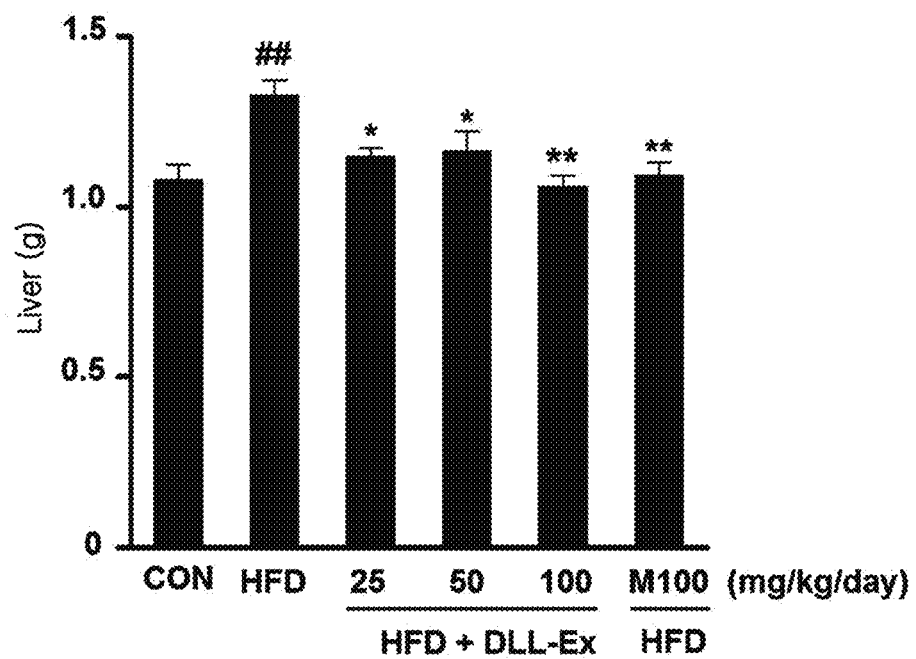
Figure 11A:
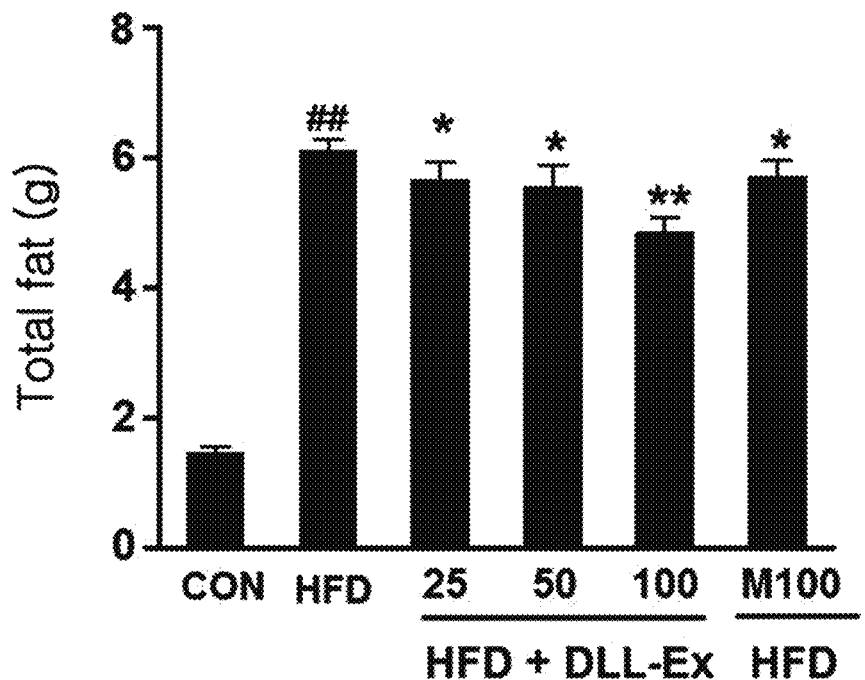
FIGS. 11A to 11D show results obtained by evaluating effects of 25, 50 and 100 (mg/kg/day) of the hot water extract of *Dolichos lablab* Linne with respect to a high-fat diet on weights of the total fat (FIG. 11A), the abdominal subcutaneous fat (FIG. 11B), the epididymal fat tissue (FIG. 11C), and the small intestine fat tissue (FIG. 11D), of mice. ## indicates that the weights of the total fat (FIG. 11A), abdominal subcutaneous fat (FIG. 11B), epididymal fat tissue (FIG. 11C), and small intestine fat tissue (FIG. 11D), of the high-fat dietary group (HFD) are significantly increased compared to that of the normal control group (CON)(p<0.01), and * and  indicate that the weights of the total fat (FIG. 11A), abdominal subcutaneous fat (FIG. 11B), epididymal fat tissue (FIG. 11C) and small intestine fat tissue (FIG. 11D**) of the experimental group (HFD+DLL-Ex) receiving high-fat diet and the hot water extract of *Dolichos lablab* Linne are significantly decreased compared to that of the high-fat dietary group (HFD). M100 is a positive control group, which is administered with Milk Thistle extract (100 mg/kg/day) together with a high-fat diet.
Figure 11B:
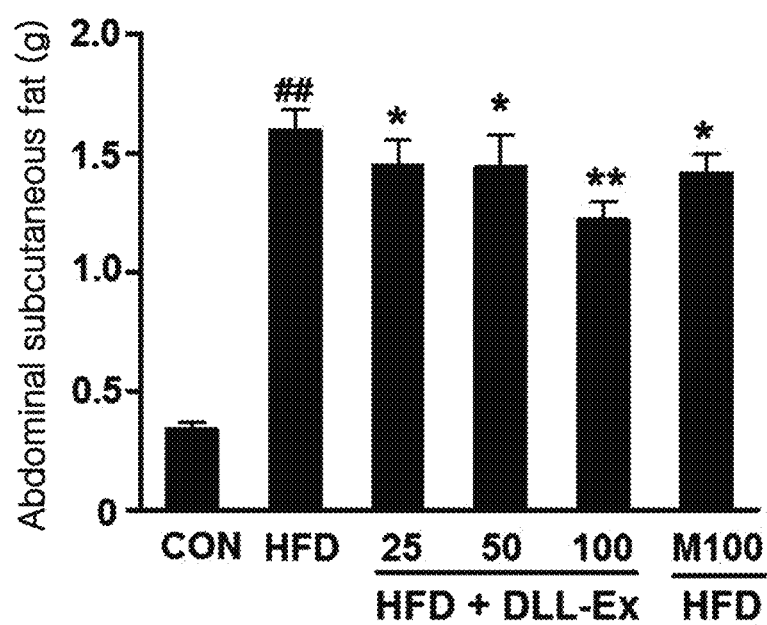
Figure 11C:
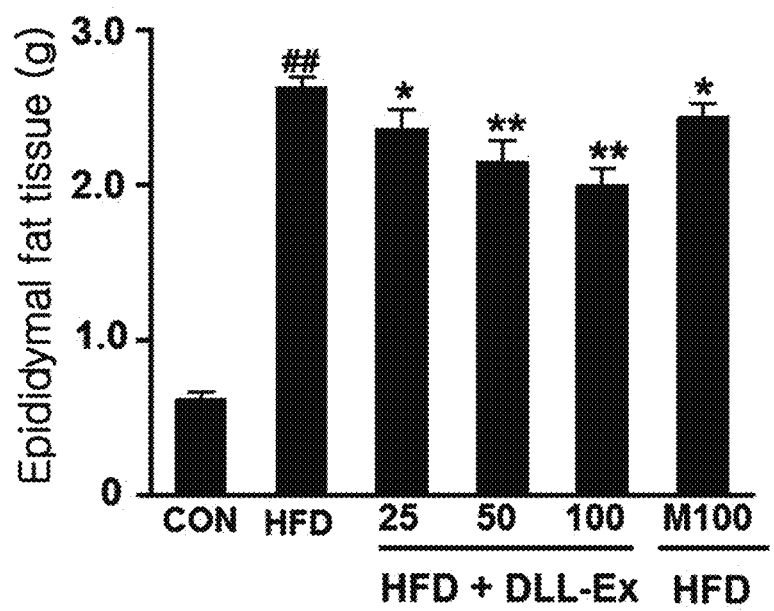
Figure 11D:
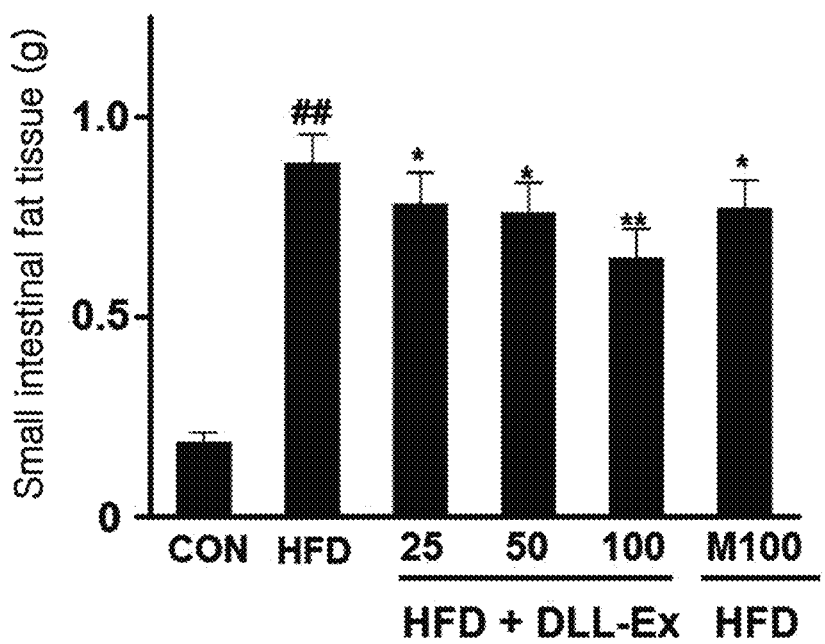

Long-term intake of high-fat diets leads to non-alcoholic fatty liver. In this experiment, it was confirmed that the liver tissue weight of the high-fat dietary group (HFD) fed with high-fat diets was significantly increased compared with the liver tissue weight of the normal control group (CON), and the group receiving the high-fat diet and administered with the hot water extract of *Dolichos lablab* Linne showed a substantially small liver tissue weight. In particular, the weight of liver tissue was significantly low in the group treated with the high-fat diet and 100 mg/kg/day of the *Dolichos lablab* Linne (FIG. 10B). This result supports the effect that the hot water extract of *Dolichos lablab* Linne prevents fat accumulation in the liver tissue induced by a high-fat diet.

The effects of the hot water extract of *Dolichos lablab* Linne according to the present invention on the increase in total fat, abdominal subcutaneous fat, epididymal fat tissue, and small intestine fat tissue of the mice were evaluated. Results showed that, compared with the high-fat dietary group, the group treated with the high-fat diet and the hot water extract of *Dolichos lablab* Linne according to the present invention showed a substantial decrease in the increase in total fat, abdominal subcutaneous fat, epididymal fat tissue, and small intestine fat tissue of the mice. In particular, in the group treated with 100 mg/kg/day of the hot water extract of *Dolichos lablab* Linne, the increase in total fat, abdominal subcutaneous fat, epididymal fat tissue, and small intestine fat tissue of the mice was significantly decreased (FIGS. 11A to 11D).

These results suggest that the herbal medicine extract according to the present invention has an effect of preventing or treating obesity.

(3) ALT and AST Changes in Blood

Figure 12A:
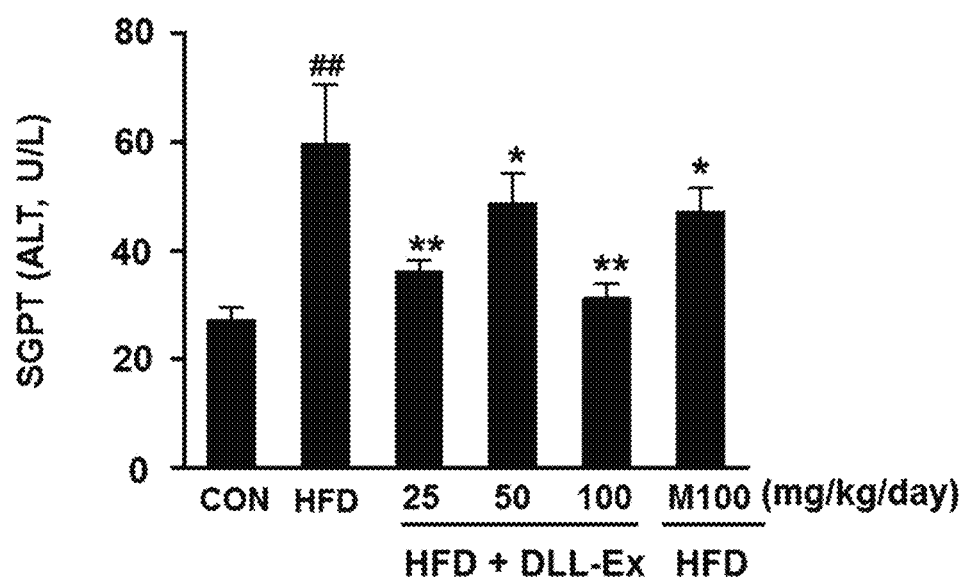
FIGS. 12A and 12B show results obtained by evaluating whether 25, 50 and 100 (mg/kg/day) of the hot water extract of *Dolichos lablab* Linne reduces an increase in ALT and AST in the blood, the increase being caused by a high-fat diet. ## indicates that ALT (FIG. 12A) and AST (FIG. 12B) in the high-fat diet fed group (HFD) are significantly increased compared to the normal chow diet fed group (CON), and * and  indicate that ALT (FIG. 12A) and AST (FIG. 12B**) in the experimental group (HFD+DLL-Ex) receiving high-fat diet and the hot water extract of *Dolichos lablab* Linne are significantly decreased compared to that of the high-fat dietary group (HFD). M100 is a positive control group, which is administered with Milk Thistle extract (100 mg/kg/day) together with a high-fat diet.
Figure 12B:
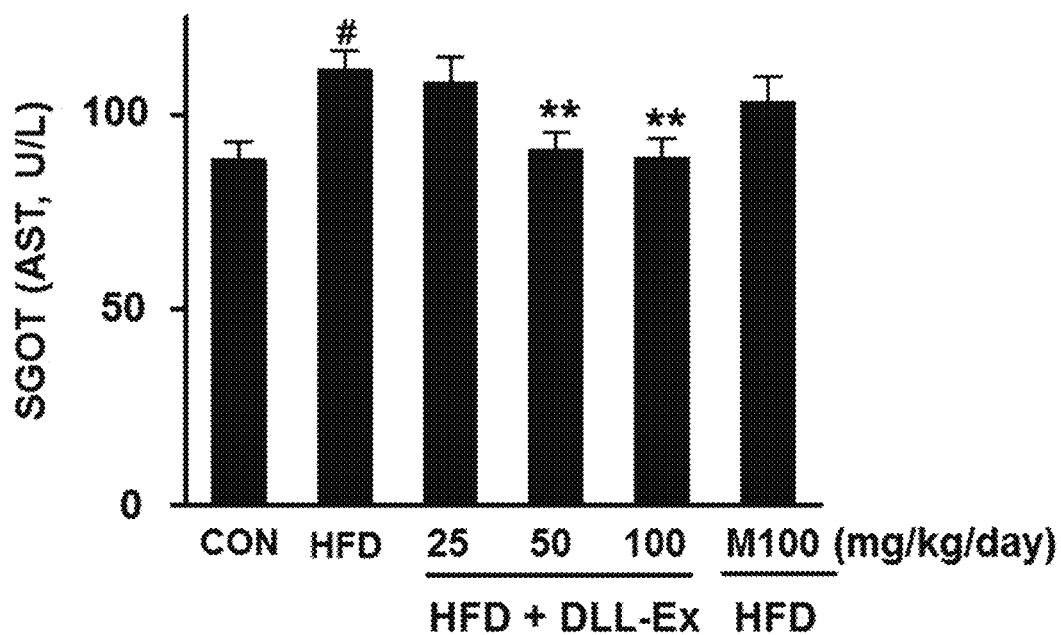
Figure 13A:
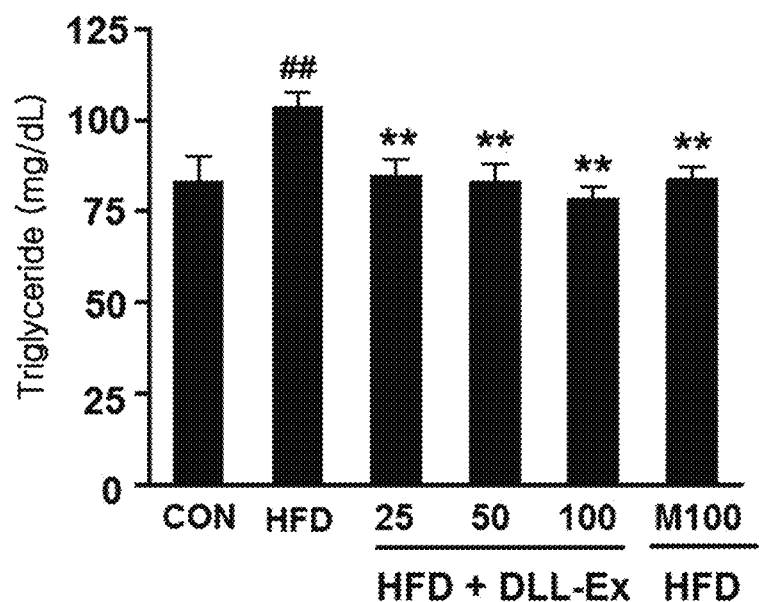
FIGS. 13A to 13D show results obtained by evaluating reducing effects of 25, 50 and 100 (mg/kg/day) of the hot water extract of *Dolichos lablab* Linne on an increase in triglyceride (FIG. 13A), total cholesterol (FIG. 13B), low density lipoprotein (FIG. 13C), and free fatty acid (FIG. 13D) in the blood, the increase being caused by a high-fat diet. ## indicates that the triglyceride (FIG. 13A), total cholesterol (FIG. 13B), low density lipoprotein (FIG. 13C), and free fatty acid (FIG. 13D) of the high-fat diet fed group (HFD) in the blood are significantly increased compared to that of the normal chow diet fed control group (CON) (p<0.01), and * and  indicate that the triglyceride (FIG. 13A), total cholesterol (FIG. 13B), low density lipoprotein (FIG. 13C), and free fatty acid (FIG. 13D**), of the experimental group (HFD+DLL-Ex) having high-fat diet intake and the hot water extract of *Dolichos lablab* Linne in the blood are significantly decreased compared to that of the high-fat diet fed group (HFD). M100 is a positive control group, which is administered with Milk Thistle extract (100 mg/kg/day) together with a high-fat diet.
Figure 13B:
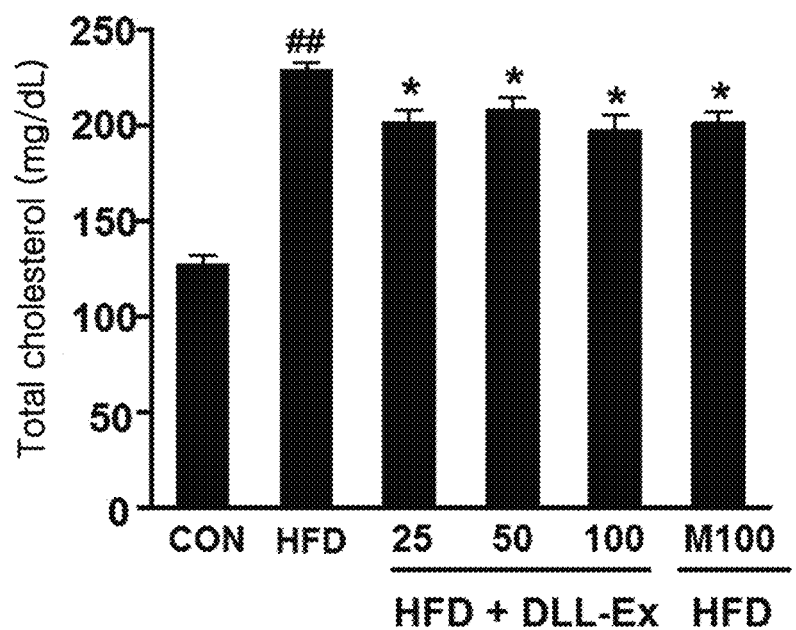
Figure 13C:
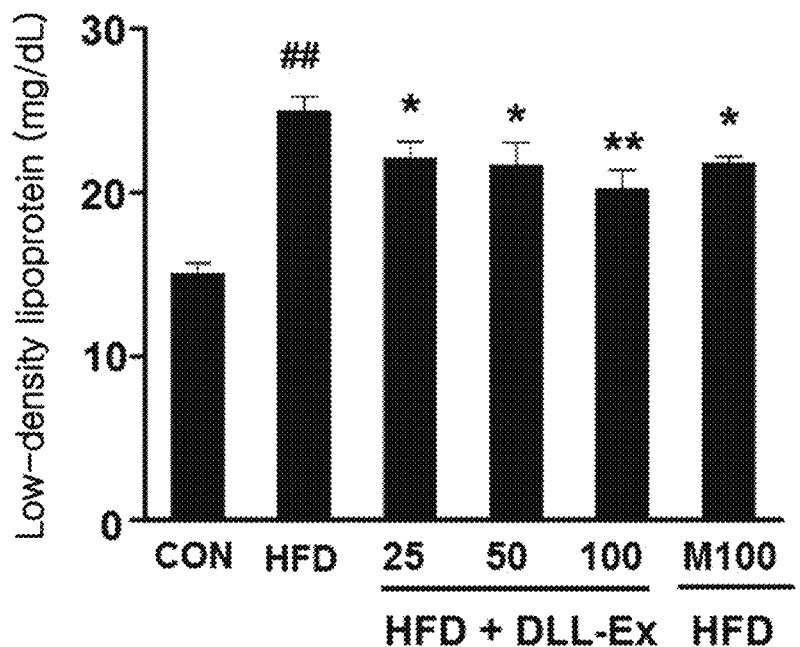
Figure 13D:
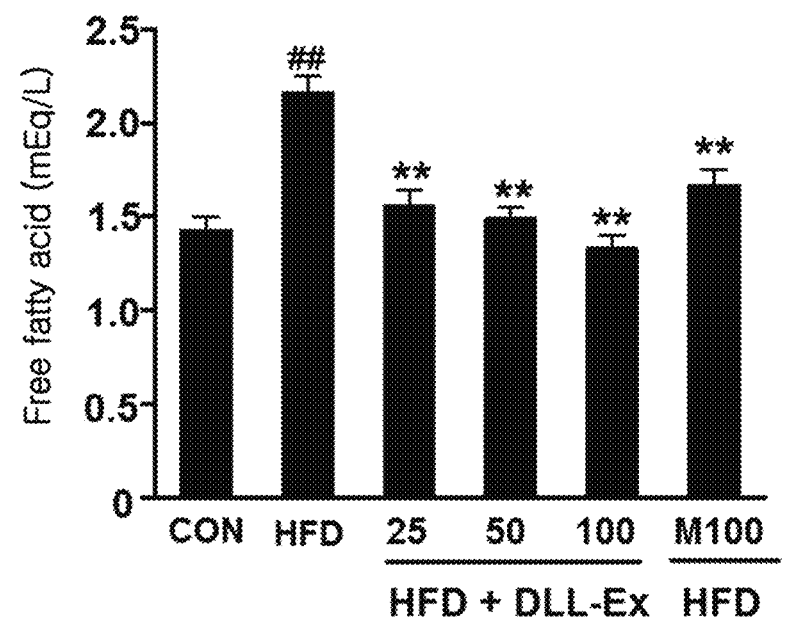

The effects of the hot water extract of *Dolichos lablab* Linne according to the present invention on the increase in ALT and AST in the blood due to the high-fat diet was evaluated. Results showed that, compared with the high-fat dietary group, the group treated with the high-fat diet and the hot water extract of *Dolichos lablab* Linne prepared in (1) of Example 3 showed a significant decrease in ALT and AST (FIGS. 12A and 12B).

These results indicate that the dietary addition of the hot water extract of *Dolichos lablab* Linne according to the present invention reduces SGPT (ALT) and SGOT (AST) enzyme activities in the blood, suggesting that the herbal medicine extract according to the present invention improves a non-alcoholic fatty liver caused by the high-fat diet to inhibit liver damage.

(4) Change in Triglyceride, Total Cholesterol, Low-Density Lipoprotein, Free Fatty Acid in Blood Whether the hot water extract of *Dolichos lablab* Linne prepared in (1) of Example 3 according to the present invention reduces the increase in triglyceride, total cholesterol, low-density lipoprotein, and free fatty acid levels in the blood caused by the high-fat diet was evaluated. Results showed that the substantially increased triglyceride, total cholesterol, low-density lipoprotein, and free fatty acid levels in the high-fat dietary group were decreased in a relatively concentration-dependent manner in the group administered with hot water extract of *Dolichos lablab* Linne (FIGS. 13A to 13D).

Therefore, it was confirmed that the dietary supplementation of the hot water extract of *Dolichos lablab* Linne significantly reduced the lipid levels in the blood and improved the non-alcoholic fatty liver induced by the high-fat diet.

(5) Change in Concentration of Fasting Blood Sugar

Figure 14:
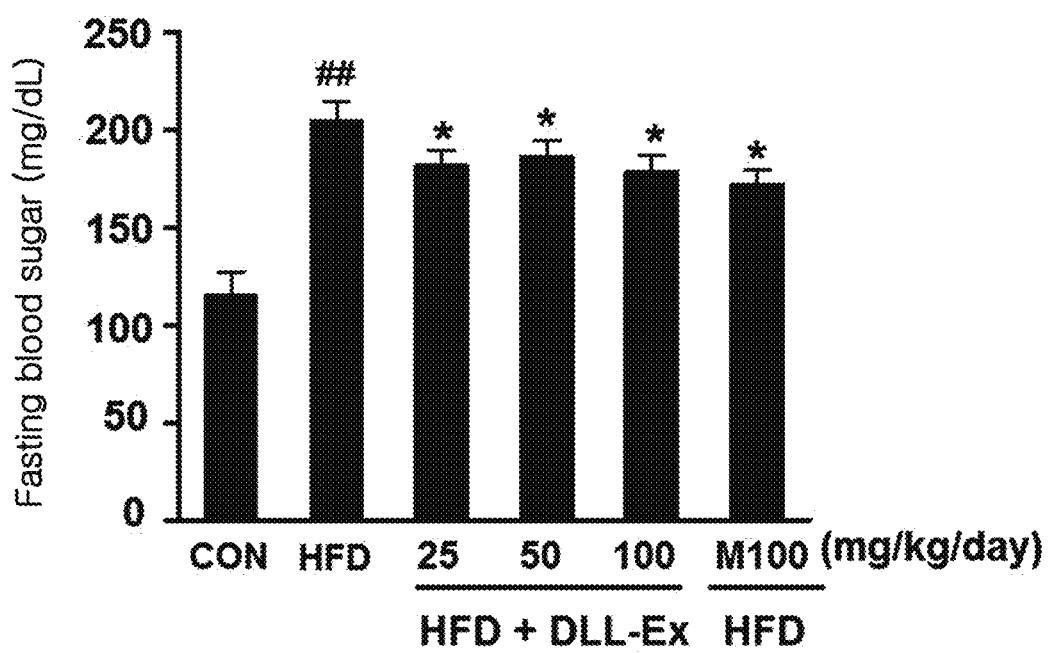
FIG. 14 shows results obtained by evaluating whether 25, 50 and 100 (mg/kg/day) of the hot water extract of *Dolichos lablab* Linne reduces an increase in the fasting blood sugar level which is caused by a high-fat diet. ## indicates that the fasting blood sugar level of the high-fat dietary group (HFD) is significantly increased compared to that of the normal chow diet fed control group (CON) ($p<0.01$), and * and ** indicate that the fasting blood sugar level of the experimental group (HFD+DLL-Ex) receiving high-fat diet and the hot water extract of *Dolichos lablab* Linne is significantly decreased compared to that of the high-fat dietary group (HFD). M100 is a positive control group, which is administered with Milk Thistle extract (100 mg/kg/day) together with a high-fat diet.

The effects of the hot water extract of *Dolichos lablab* Linne according to the present invention on the decrease in sugar concentration in blood increased due to the high-fat diet was evaluated. Results showed that, compared with the high-fat dietary group, the group treated with the high-fat diet and the hot water extract of *Dolichos lablab* Linne according to the present invention showed a significant decrease in glucose concentration in blood (FIG. 14).

Therefore, it was confirmed that the dietary addition of the hot water extract of *Dolichos lablab* Linne according to the present invention significantly decreases the sugar concentration in the serum.

What is to be claimed is:

1. A method of treating non-alcoholic fatty liver disease or reducing a symptom of the non-alcoholic fatty liver disease, the method comprising administering a composition to a subject having the non-alcoholic fatty liver disease or the symptom, wherein the composition consists of an extract of *Dolichos lablab* Linne and optionally at least one of a pharmaceutically acceptable carrier and a pharmaceutically acceptable adjuvant.

2. The method of claim 1, wherein the extract of *Dolichos lablab* Linne is a hot water extract of *Dolichos lablab* Linne.

3. The method of claim 1, wherein an amount of the extract of the *Dolichos lablab* Linne is in a range of 0.1 wt % to 10 wt % based on the total weight of the composition.

4. The method of claim 1, further comprising determining a total dosage of the extract of the *Dolichos lablab* Linne by monitoring triglyceride content in liver tissue of the subject.

5. The method of claim 1, wherein the non-alcoholic fatty liver disease is any one selected from non-alcoholic simple fatty liver, non-alcoholic fatty hepatitis, and non-alcoholic liver cirrhosis.

6. The method of claim 1, wherein the composition is a pharmaceutical composition.

7. The method of claim 6, wherein the composition consists of the extract of *Dolichos lablab* Linne and the pharmaceutically acceptable carrier selected from the group consisting of a saline solution, Ringer's solution, buffered saline solution, dextrose solution, maltodextrin solution, glycerol, ethanol, lactose, dextrose, sucrose, sorbitol, mannitol, starch, acacia rubber, calcium phosphate, alginate, gelatin, calcium silicate, microcrystalline cellulose, polyvinylpyrrolidone, cellulose, syrup, methylcellulose, methylhydroxybenzoate, propylhydroxybenzoate, talc, magnesium stearate, mineral oil, and a combination thereof.

8. The method of claim 6, wherein the composition consists of the extract of *Dolichos lablab* Linne and the pharmaceutically acceptable adjuvant selected from the group consisting of an antioxidant, a bacteriostatic agent, a surfactant, a binder, a lubricant, a wetting agent, a sweetener, a flavoring agent, an emulsifier, a suspending agent, a preservative, and a combination thereof.

9. The method of claim 1, wherein the subject is human.

10. A method of treating non-alcoholic fatty liver disease or reducing a symptom of the non-alcoholic fatty liver disease, the method comprising administering a composition comprising an extract of *Dolichos lablab* Linne to a human having the non-alcoholic fatty liver disease or the symptom, wherein the total dosage per day of the extract of the *Dolichos lablab* Linne is at least 8.1 mg per kilogram of the weight of the human.

11. A method of treating a symptom caused by increased body weight or increased blood sugar elevated by a high-fat diet, the method comprising administering a composition to a subject having the symptom, wherein the composition consists of an extract of *Dolichos lablab* Linne and optionally at least one of a pharmaceutically acceptable carrier and a pharmaceutically acceptable adjuvant.

12. The method of claim 11, wherein the subject has diabetes.

13. The method of claim 11, wherein the extract of *Dolichos lablab* Linne is a hot water extract of *Dolichos lablab* Linne.

14. The method of claim 11, wherein an amount of the extract of the *Dolichos lablab* Linne is in a range of 0.1 wt % to 10 wt % based on the total weight of the composition.

15. The method of claim 11, wherein the composition consists of the extract of *Dolichos lablab* Linne and the at least one pharmaceutically acceptable carrier selected from a saline solution, Ringer's solution, buffered saline solution, dextrose solution, maltodextrin solution, glycerol, ethanol, lactose, dextrose, sucrose, sorbitol, mannitol, starch, acacia rubber, calcium phosphate, alginate, gelatin, calcium silicate, microcrystalline cellulose, polyvinylpyrrolidone, cellulose, syrup, methylcellulose, methylhydroxybenzoate, propylhydroxybenzoate, talc, magnesium stearate, and mineral oil.

16. The method of claim 11, wherein the composition consists of the extract of *Dolichos lablab* Linne and the at least one pharmaceutically acceptable adjuvant selected from an antioxidant, a buffer, a bacteriostatic agent, a surfactant, a binder, a lubricant, a wetting agent, a sweetener, a flavoring agent, an emulsifier, a suspending agent, and a preservative.

17. The method of claim 11, wherein the subject is human.

18. The method of claim 1, wherein the composition is a formulation of a capsule or a tablet.

* * * * *